United States Patent
Sharif et al.

(10) Patent No.: US 10,736,727 B2
(45) Date of Patent: Aug. 11, 2020

(54) SELF STACKABLE AND INTERLOCKING PACKAGING

(71) Applicant: ALPHA BIO TEC. LTD., Petach Tikva (IL)

(72) Inventors: Eitan Sharif, Kibbutz Gesher-Haziv (IL); Assaf Sharon, Tel Aviv (IL); Eilam Oron, Shoham (IL)

(73) Assignee: ALPHA BIO TEC. LTD., Petach Tikva (IL)

( * ) Notice: Subject to any disclaimer, the term of this patent is extended or adjusted under 35 U.S.C. 154(b) by 108 days.

(21) Appl. No.: 15/553,831

(22) PCT Filed: Mar. 8, 2016

(86) PCT No.: PCT/IL2016/050256
§ 371 (c)(1),
(2) Date: Aug. 25, 2017

(87) PCT Pub. No.: WO2016/142939
PCT Pub. Date: Sep. 15, 2016

(65) Prior Publication Data
US 2018/0243070 A1    Aug. 30, 2018

(30) Foreign Application Priority Data
Mar. 9, 2015 (IL) .......................... 237633

(51) Int. Cl.
*A61F 2/00* (2006.01)
*A61C 8/00* (2006.01)
(Continued)

(52) U.S. Cl.
CPC ............ *A61F 2/0095* (2013.01); *A61B 50/00* (2016.02); *A61B 50/30* (2016.02); *A61C 8/0087* (2013.01);
(Continued)

(58) Field of Classification Search
CPC ... A61B 50/00; A61B 50/30; A61B 2050/005; A61B 2050/006; A61B 2050/0067;
(Continued)

(56) References Cited

U.S. PATENT DOCUMENTS 3,578,158 A * 5/1971 Aylott .................... B65D 25/10
206/509
3,743,088 A   7/1973 Henkin
(Continued)

FOREIGN PATENT DOCUMENTS

| EP | 1 481 905 A1 | 12/2004 |
|---|---|---|
| JP | 2008 105725 A | 5/2008 |
| UA | 41337 C2 | 4/1995 |

OTHER PUBLICATIONS

International Application Search Report dated Sep. 30, 2016 for International Application No. PCT/IL2016/050256 filed Mar. 8, 2016 in 6 pages.

*Primary Examiner* — Bryon P Gehman
(74) *Attorney, Agent, or Firm* — Knobbe, Martens, Olson & Bear, LLP

(57) ABSTRACT

The present invention relates to packaging and in particular, to sterile packaging that is configured to be self-stackable and interlocking. A sterile packaging comprising a packaging compartment provided having one open face through which the compartment may be filled, the open face forms a sterile sealing face that is to be sealed with and receive a sterile barrier. The package features at least one coupling interface along an external surface having male to female couplers configured to facilitate piggy-back coupling between two packaging.

18 Claims, 10 Drawing Sheets

(51) Int. Cl.
  *A61B 50/30* (2016.01)
  *A61C 19/02* (2006.01)
  *A61B 50/00* (2016.01)

(52) U.S. Cl.
  CPC ........ *A61C 19/02* (2013.01); *A61B 2050/005* (2016.02); *A61B 2050/006* (2016.02); *A61B 2050/0067* (2016.02); *A61B 2050/3007* (2016.02); *A61B 2050/3009* (2016.02); *A61C 2202/00* (2013.01)

(58) Field of Classification Search
  CPC .... A61B 2050/3007; A61B 2050/3009; A61C 8/00; A61C 8/0087; A61C 19/02; A61C 2202/00; A61F 2/00; A61F 2/0095
  USPC ................................ 206/63.5, 504, 509, 511
  See application file for complete search history.

(56) References Cited

U.S. PATENT DOCUMENTS

| | | | | |
|---|---|---|---|---|
| 3,853,217 | A * | 12/1974 | Scordato | B01L 9/543 |
| | | | | 206/503 |
| 5,366,088 | A * | 11/1994 | Hill | B01L 9/543 |
| | | | | 206/509 |
| 8,770,409 | B2 * | 7/2014 | Cude | B65D 21/0204 |
| | | | | 206/363 |
| 8,875,873 | B2 * | 11/2014 | Cinader, Jr. | A61C 7/14 |
| | | | | 206/368 |
| 9,173,463 | B2 * | 11/2015 | Clamp | A45C 11/005 |
| 2012/0118848 | A1 | 5/2012 | Hendrickson et al. | |
| 2014/0202908 | A1 | 7/2014 | Liburd et al. | |

\* cited by examiner

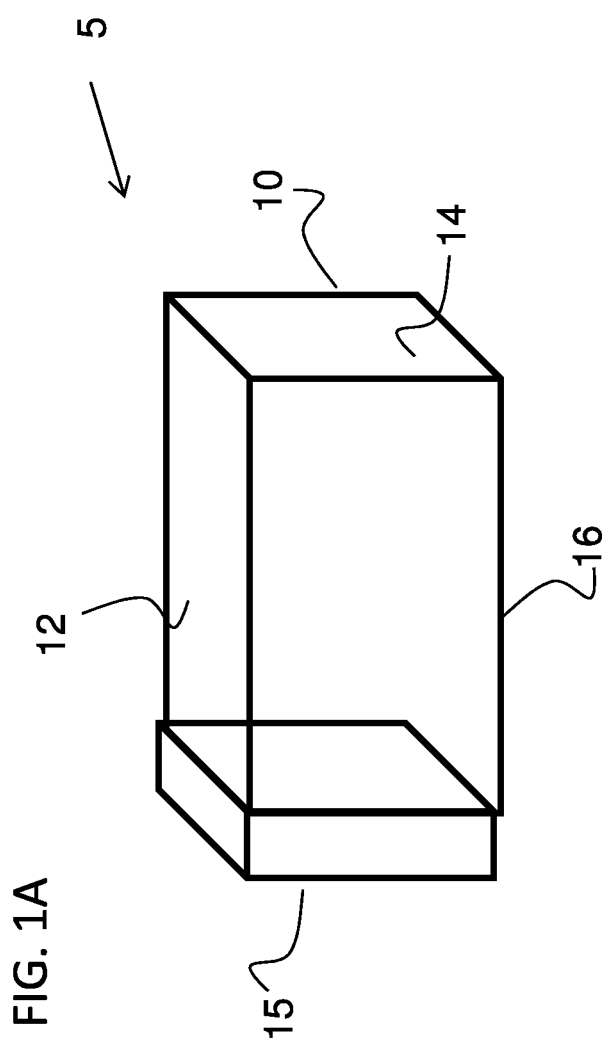

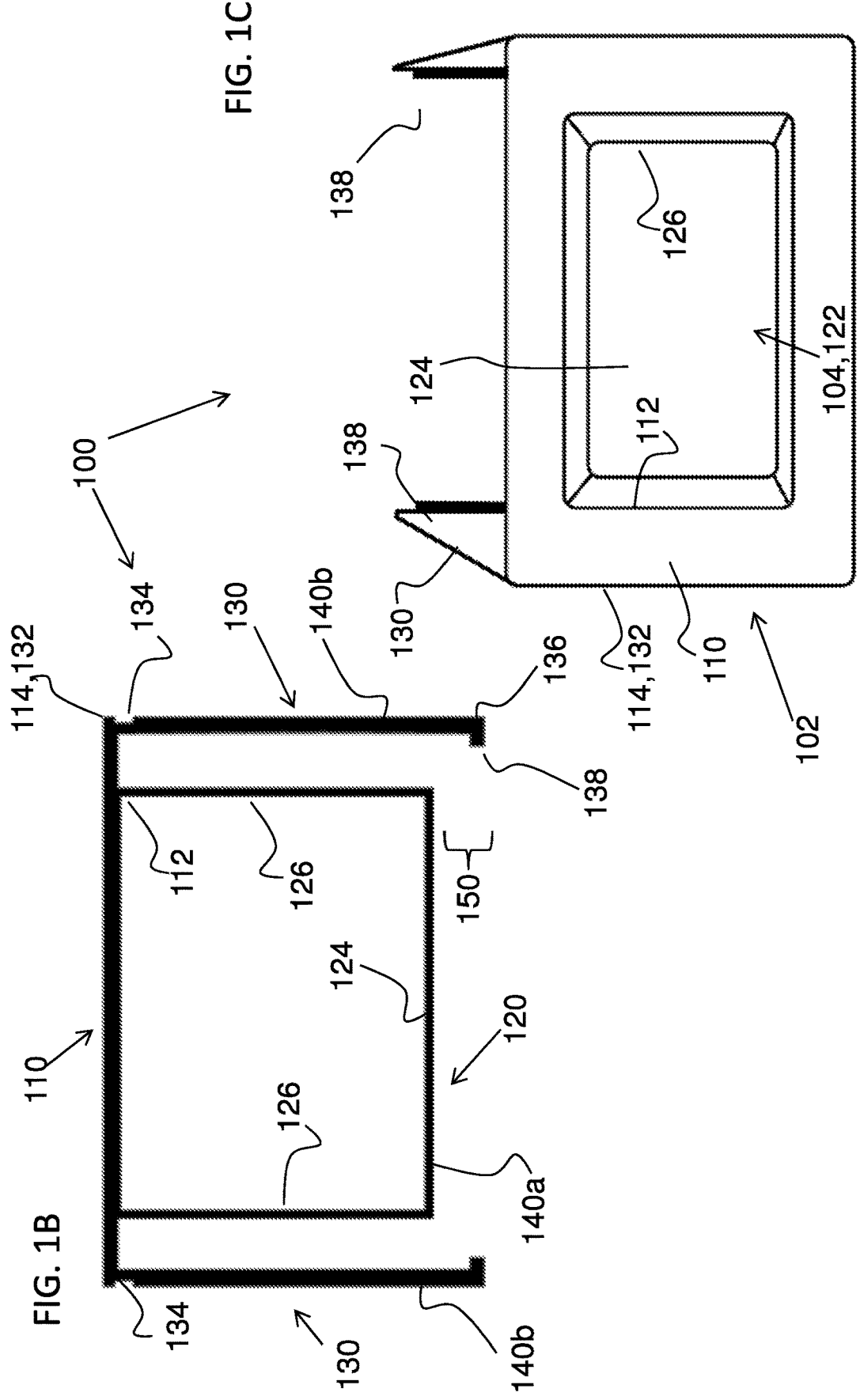

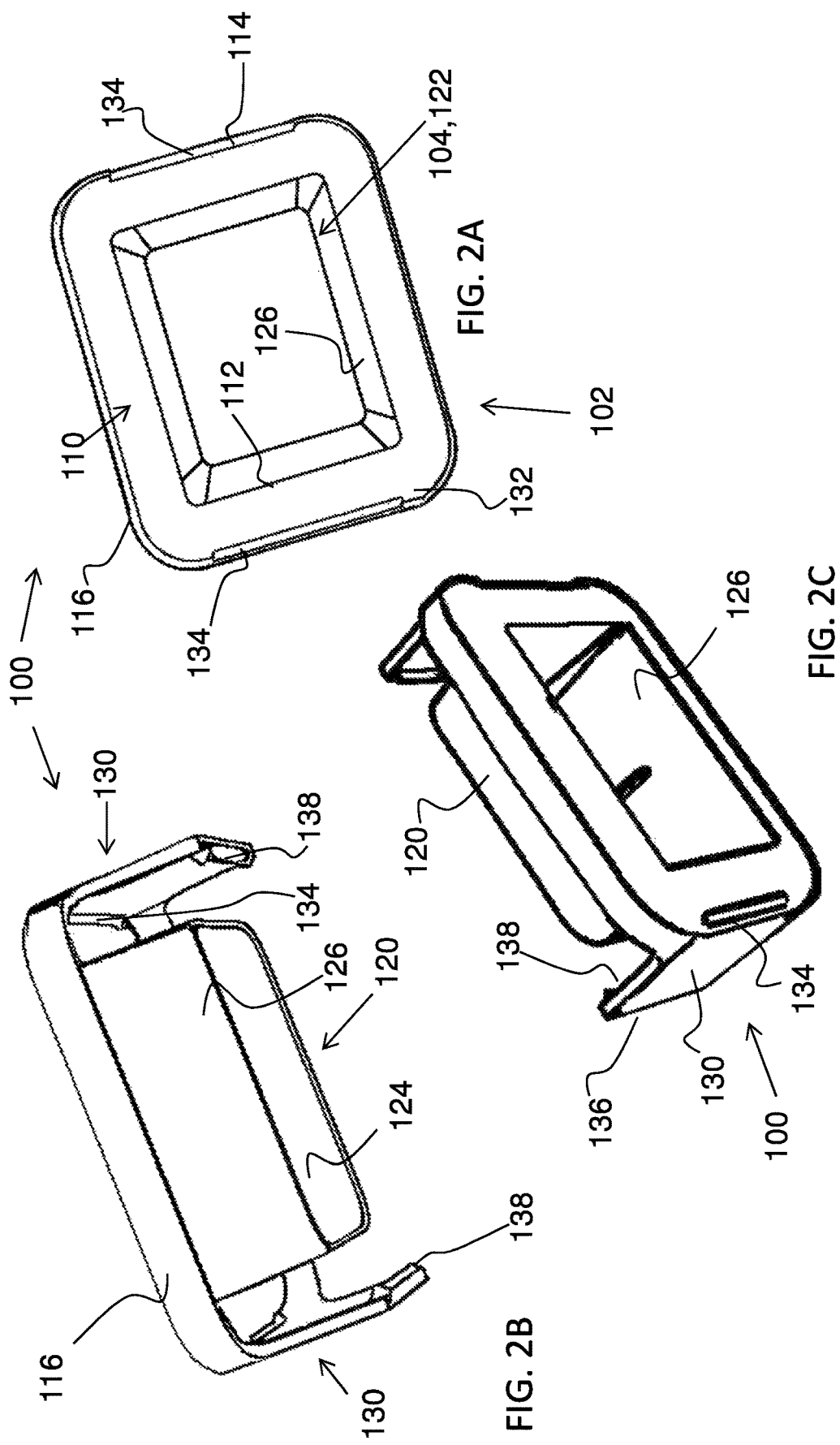

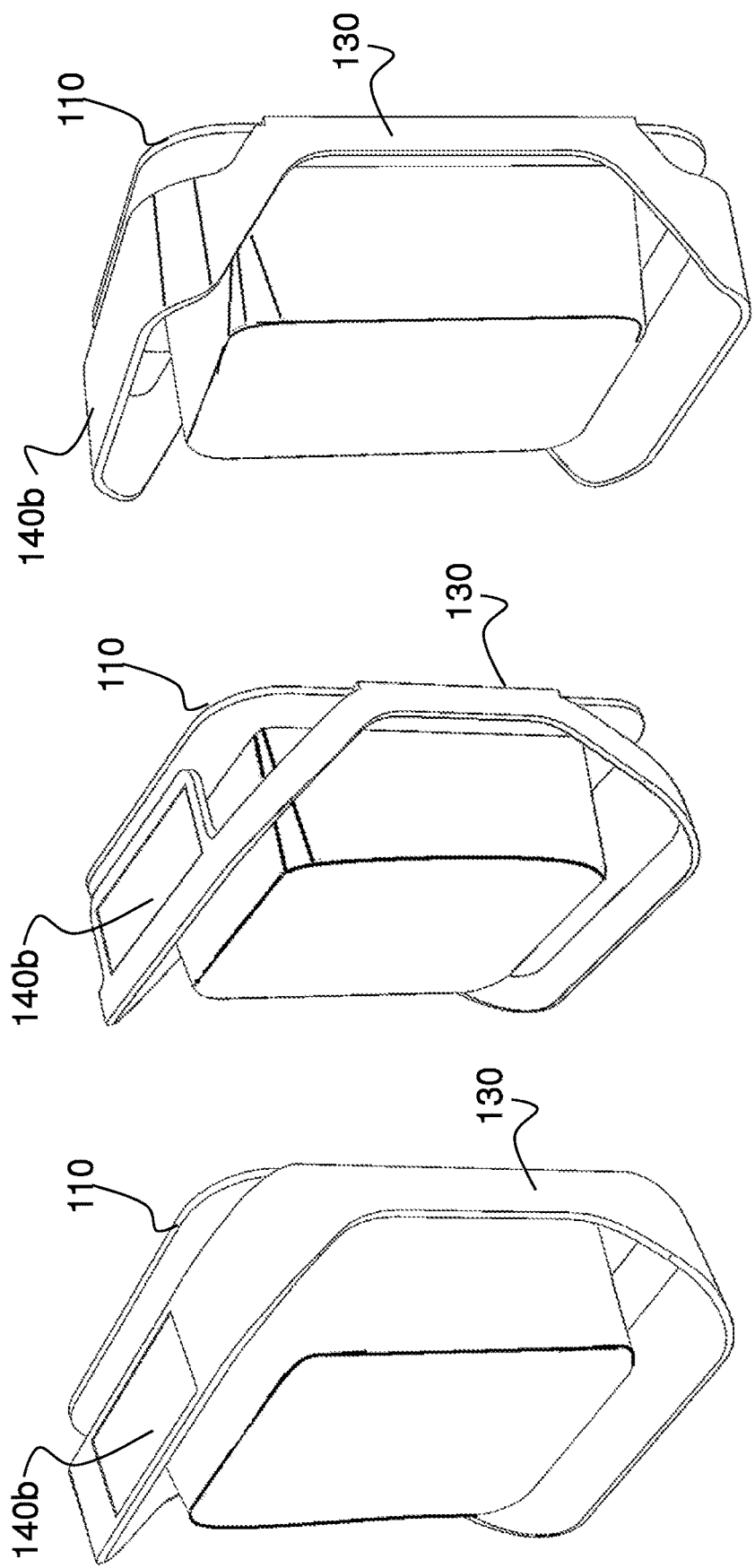

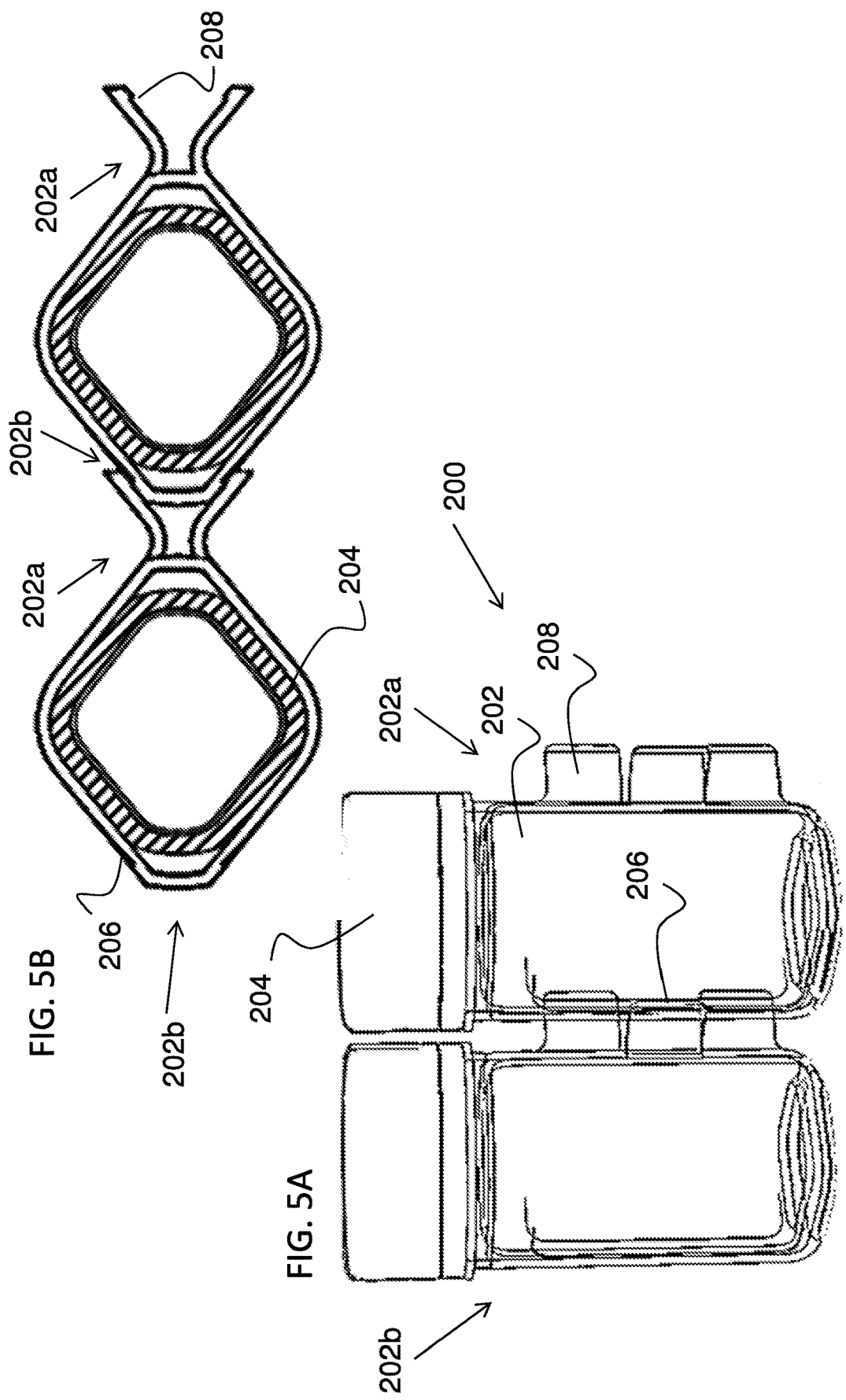

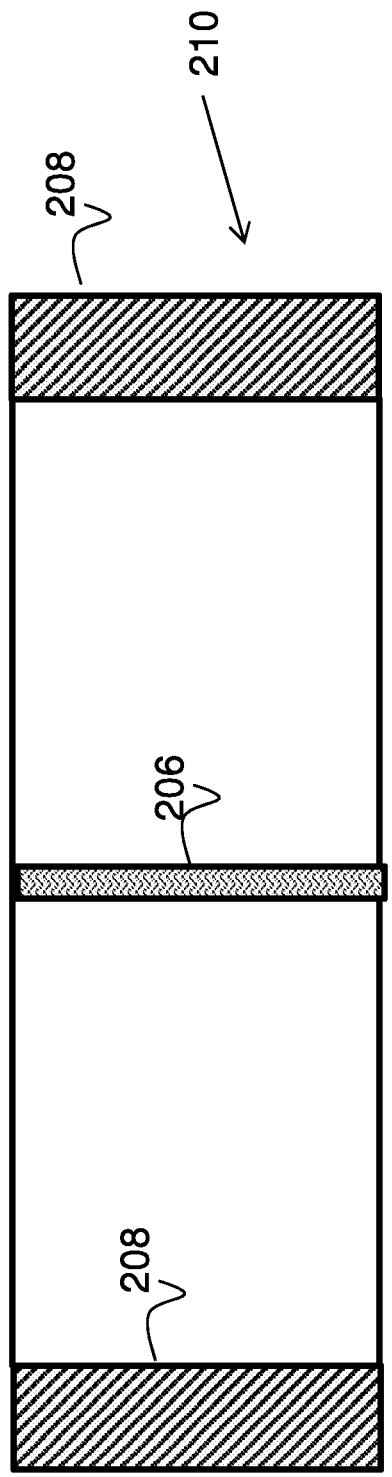
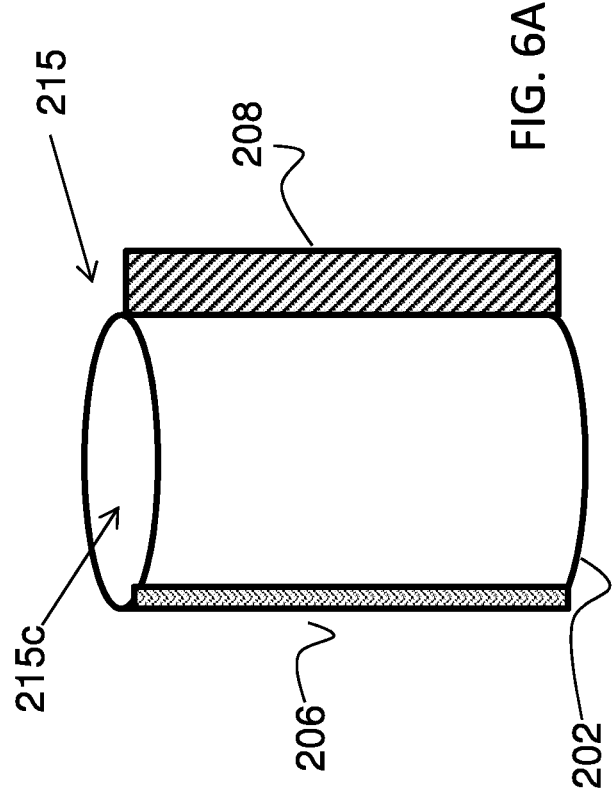
FIG. 6B
FIG. 6A

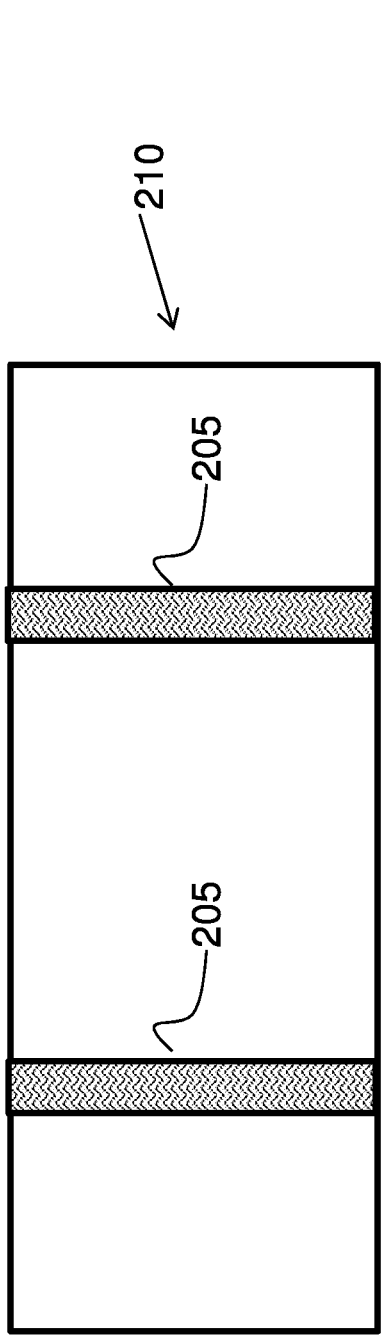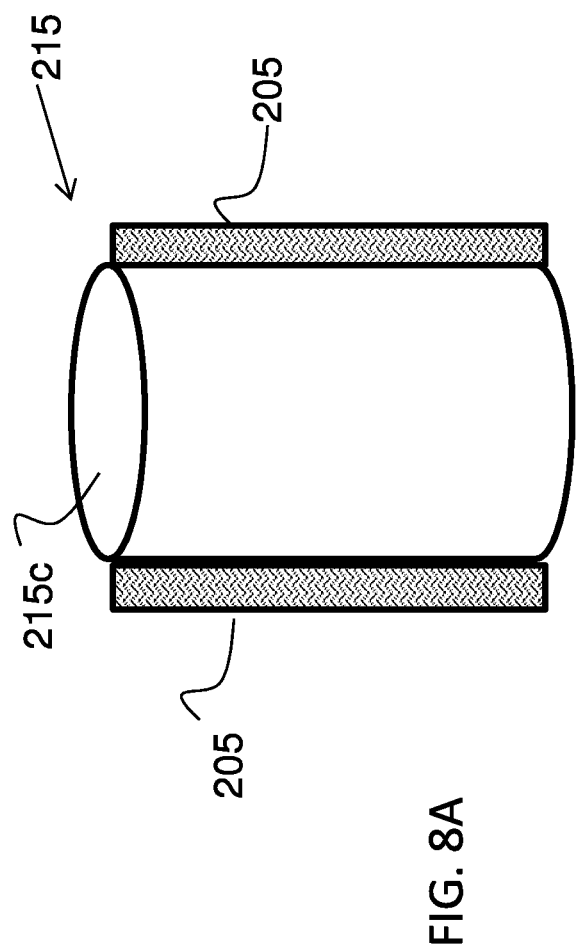

SELF STACKABLE AND INTERLOCKING PACKAGING

CROSS-REFERENCE TO RELATED APPLICATIONS

This application is a national stage application under 35 U.S.C. § 371 of International Application No. PCT/IL2016/050256, filed on Mar. 8, 2016, which published in English as WO 2016/142939 A2 on Sep. 15, 2016 and which claims priority benefit of Israeli Patent Application No. 237633 filed on Mar. 9, 2015.

FIELD OF THE INVENTION

The present invention relates to packaging and in particular, to sterile packaging that is configured to be self-stackable and interlocking.

BACKGROUND OF THE INVENTION

The storage and accessibility of medical implants can help to facilitate the sorting, storing, locating and handling of the implants. Currently, implants packages are individually deposited in a box, or positioned on a board, in a drawer, on a peg. This system of depositing, used by current packaging, is cumbersome and difficult, particularly when handling several implant packages at the same time. This leads to non-optimal use of available storage space. Further, current packaging is time-consuming in various aspects including organizing, arranging, storing, identify and gaining access to particular packaging within the storage area. Furthermore, current packaging requires large area for storing the implants, an area that may be minimized and/or optimized.

SUMMARY OF THE INVENTION

The present invention overcomes these deficiencies of the background by providing a sterile self-stackable and interlocking packaging for medical devices. The packaging according to embodiments of the present invention allows for stacking and interlocking two or more packages in a piggy-back manner. Such piggy-back stacking allows both for organizing therein minimizing storage space required while making a user aware of the packaging contents along at least one surface and more preferably along at least two or more surfaces.

Packaging according to embodiments of the present invention provide a protective buffer zone provided for protecting the packaging's sterile barrier, for example in the form of Tyvek™ which is the first and most important line of sterile protection for medical implants.

The self-stackable and interlocking packaging according to embodiments of the present invention provide a user with the ability to arrange all different implants packaging within the available storage area, which may include a drawer, suitcase or the like. Furthermore, the packaging according to the present invention provide for handling, locating the packaging in a quick manner by providing at least two visual surfaces to readily identify the contents of the packaging.

Unless otherwise defined, all technical and scientific terms used herein have the same meaning as commonly understood by one of ordinary skill in the art to which this invention belongs. The materials, methods, and examples provided herein are illustrative only and not intended to be limiting. Implementation of the method and system of the present invention involves performing or completing certain selected tasks or steps manually, automatically, or a combination thereof.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1A is a schematic block diagram of a packaging according to an optional embodiment of the present invention;

FIG. 1B-C are different views of a schematic block diagram of the packaging according to an optional embodiment of the present invention;

FIG. 2A-C are schematic illustrative diagrams of the packaging according to an optional embodiment of the present invention;

FIG. 4A-C are schematic illustrative diagrams of the packaging according to an optional embodiment of the present invention;

FIG. 5A-B are different views of a schematic illustrative diagram of embodiments for a packaging according to embodiments of the present invention;

FIG. 6A-B are schematic block diagram of embodiments for a packaging according to embodiments of the present invention;

FIG. 8A-B are schematic block diagram of embodiments for a packaging according to embodiments of the present invention.

DESCRIPTION OF THE PREFERRED EMBODIMENTS

Figure 3A:
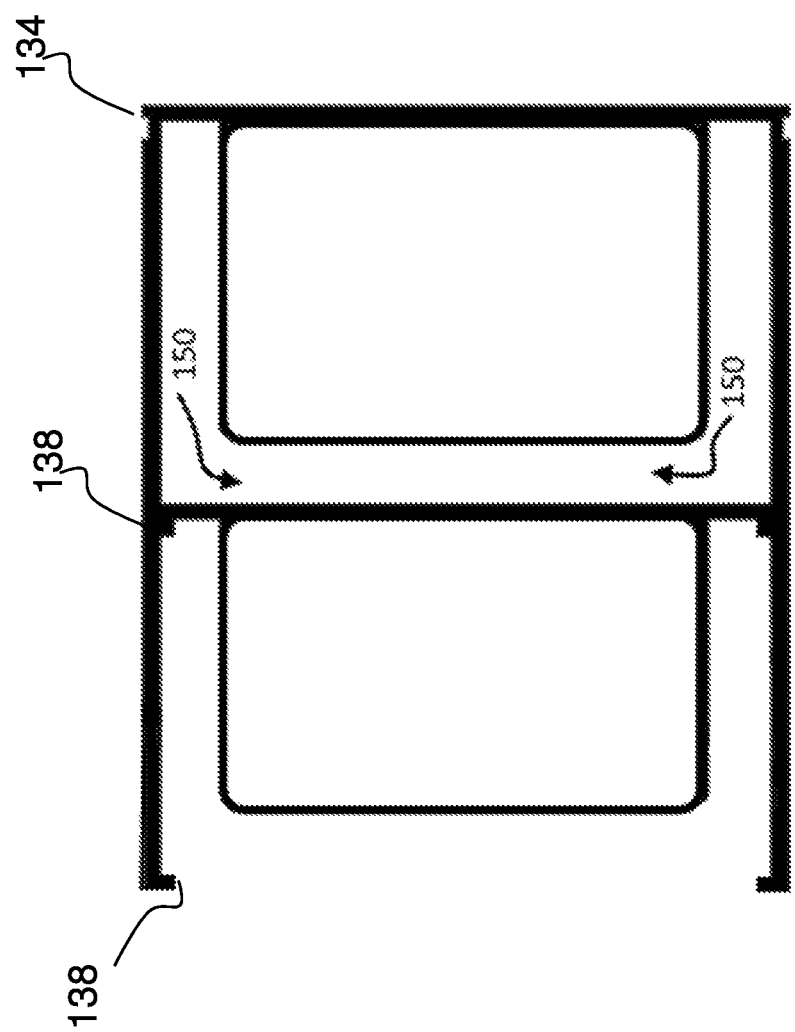
FIG. 3A-C show different views of the packaging according an embodiment of the present invention, displaying the stacked configuration assuming a piggy-back coupling configuration according to an optional embodiment of the present invention.

The principles and operation of the present invention may be better understood with reference to the drawings and the accompanying description.

The following figure reference labels are used throughout the description to refer to similarly functioning components used throughout the specification hereinbelow.

5 packaging;
10 packaging container;
12 sterile seal face;
14 perpendicular face;
15 coupling interface;
16 parallel face;
100 packaging;

102 sterile sealing face;
104 central opening;
106 sterile barrier;
110 frame body;
112 frame inner edge;
114 frame outer edge;
116 frame skirt;
120 packaging compartment;
122 compartment open sealing face;
124 compartment front surface;
126 compartment side walls;
130 supports surface;
132 support posterior edge;
134 posterior coupling member;
136 support anterior edge;
138 anterior coupling member;
140a,b product display area;
150 sterile barrier buffer zone;
200 sterile vial;
202 vial body;
203 vial body sealing face;
204 vial cap;
205 coupling member;
206 female coupling member portion;
208 male coupling member portion;
210 vial body external retrofit cover;
215 vial body sleeve retrofit housing;
215c central borehole receiving recess;

FIG. 1A shows a schematic block diagram of a packaging 5 according to an optional embodiment of the present invention. Packaging 5 comprises a container 10 having a coupling interface 15 configured to facilitate piggy back coupling between two packaging 5 and a sterile barrier face 12 configured to receive a sterile barrier for sealing the contents of container 10. As shown, sterile packaging 5 comprises a packaging compartment 10, provided for receiving and holding the contents of the packaging 5. Compartment 10 having a body defining an external surface and an internal open volume for receiving the packaged contents, the body having one open face 12 through which the compartment may be filled with the packaged contents. The open face 12 forming a sterile sealing face configured to be sealed with and receive a sterile barrier. The external surface of the packaging body featuring at least one coupling interface 15 having male to female couplers configured to facilitate piggy-back coupling between two packaging 5.

Optionally the coupling interface 15 may be disposed along the external surface of the container 10 the surface selected from a surface that is parallel 16 with respect to the sterile sealing face 12 or a surface that is perpendicular 14 with respect to the sterile sealing face 12.

Optionally the coupling interface may be provided in the form of a snap fit coupling interface comprising a female recess member and a male latch member.

Optionally packaging 5 may comprise at least two or more coupling interfaces 15 disposed on at least one or more of parallel surface 16 and/or perpendicular surface 14.

Optionally the container body may be provided in a plurality of optional shapes selected from the group consisting of vial (FIG. 5-8), cylinder, quadrilateral (FIG. 1B-4), polygon having n sides wherein n>2.

Optionally the coupling interface 15 may extends from the external surface, for example in the form of an extension (130, FIG. 1B-4) and/or arm (208, 205, FIG. 7A, 5A) as shown. Optionally coupling interface 15 may be configured along the external surface of container 10 for example along at least one or more of parallel surface 16 and/or perpendicular surface 14.

FIG. 1B-C show different views of a schematic block diagram of the packaging 100 according to the present invention. Packaging 100 is characterized in that it provides a stackable packaging that may be coupled to one another in a piggy-back manner. The piggy-back manner in which two or more packaging 100 may be coupled provides for improved organization and storage capabilities while providing a protective buffer utilized to protect the packaging's sterile barrier which that is provides a sterile seal to the packaging 100.

Preferably the packaging according to the present invention provides at least two visual surfaces to visualize the packaged item stored within package 100.

FIG. 1C shows a perspective view of packaging 100 along sterile sealing face 102. Packaging 100 is preferably configured to encase an implant for example including but not limited a dental implant vial (not shown). Preferably face 102 is configured to be sealed with a sterile barrier 106, for example including but not limited sterile barriers as is known in the art such as Tyvek™.

Packaging 100 comprises a frame body 110, packaging compartment 120 and at least two support surfaces 130. Packaging 100 is characterized in that support surface 130 provides for piggy-back coupling two packaging 100 in a front to back formation as shown in FIG. 3A-B.

Packaging 100 comprises a sterile sealing face 102 defining a sealing face of the packaging 100. Sterile sealing face 102 has a frame body 110, the frame body having central opening 104 for receiving and holding the packaged item, for example including but not limited to a dental implant.

Optionally the packaged item may be provided loose within container 120. Optionally the packaged item may be provided packaged within container 120. Optionally the packaged item may be provided within a specialized holder configured to fit within container 120.

Optionally packaging 100 may be utilized to store a dental implant that may be stored within specialized holder within container 120. For example the specialized holder for a dental implant may be provided in the form of a dental implant vial (not shown).

Frame 110 has an inner edge frame 112, an outer edge frame (114) that define a central opening 104 and the sealing face 122 of packaging compartment 120 configured to retain the contents of packaging 100.

Most preferably, frame body 110 features a frame width defined across the inner edge 112 and outer edge 112; the frame body along at least a portion of its width provides a surface onto which a sterile barrier 106 may be coupled so as to seal central opening 104 along sterile sealing face 102.

The body of compartment 120 has an open sealing face 122 where the body is defined as an extension from frame 110. Compartment 120 preferably extends anteriorly from the inner edge 112 of frame body 110 toward a front surface 124 therein defining side walls 126. The surface of side walls 126 extending anteriorly from the inner edge 112 of frame body 110 fluidly connecting frame 110 with front surface 124 therein forming the holding compartment 120 of packaging 100. The depth of side walls 126 define the depth of holding compartment 120.

Optionally and preferably front surface 124 is a substantially flat and even surface.

Packaging 100 preferably comprises at least two opposing support surfaces 130 that extend anteriorly from the outer edge 114 of frame 110. Most preferably support surfaces 130 are configured as coupling members that provide for coupling between two packaging units 100 in a piggy-back manner. Preferably support surface 130 is configured to be longer than the depth of packaging compartment 120 as defined by side walls 126, therein providing a buffer zone 150 between adjacent coupled packages.

Optionally each support surface 130 may define a substantially flat and even surface, having a posterior edge 132 and an anterior edge 136. Optionally and preferably support surface 130 provide for forming an upper (top) support surface and a lower (bottom) support surface that may be utilized as a display area, for example in the form of a secondary display area 140*b*.

Optionally support members 130 may extend from any portion of the outer edge of frame 110. For example as shown in FIG. 1-3, support members 130 extend from the short side of frame 110. For example as shown in FIG. 4A-C support members 130 may extend from the long side of frame 110. Optionally support members 130 may extend from any portion of the outer edge of frame 110 for example including but not limited to the short side (FIG. 1-3), long side (FIG. 4A-C), corners, middle portion, any combination thereof or the like.

Posterior edge 132 is continuous with the outer edge 114 of frame body 110 and includes a posterior coupling member 134 disposed adjacent outer edge 114. Optionally and preferably coupling member 134 is provided in the form of recess along at least a portion of the length of outer edge 114, for example as shown.

Anterior edge 136 includes an anterior coupling member 138 that is preferably disposed adjacent to the end of anterior edge 136. Optionally and preferably coupling member 138 is provided in the form of a male latch extension member defined along at least a portion of the length of the end of anterior edge 136, for example as shown.

Most preferably posterior coupling member 134 and anterior coupling member 138 are configured to correspond with one another therein allowing for anterior-posterior piggy-back stacking and/or coupling between two packaging units 100.

Most preferably two piggy-backed coupling units form a sequential and continuous support surface 130 along both packaging units 100 therein defining a continuous flat and even support surface.

Optionally posterior coupling member 134 may be configured to be a female coupling member; and anterior coupling member 138 may be configured to be a corresponding male coupling member.

Optionally and preferably posterior coupling member 134 is configured to be a recess along the outer edge 114 at posterior edge 132 and anterior coupling member 138 is configured to be a male latch member, for example as shown, having dimensions corresponding recess 134.

Optionally posterior coupling member 134 may be configured to be a male coupling member; and anterior coupling member 138 may be configured to be a corresponding female coupling member.

Optionally frame 110 may be configured to have a substantially quadrilateral configuration, for example as shown. Optionally and preferably as shown in FIG. 2A-C frame 110 may be configured to have a substantially rectangular configuration including two parallel long sides and two parallel short sides, wherein support surfaces 130 extend anteriorly from the outer edge 114 of each of the two parallel short sides, for example as shown in FIG. 2A-C.

Optionally packaging 100 may comprise at least four packaging supports 130 extending from a portion along the length of outer edge 114.

Optionally and preferably support 130 are disposed along the length of outer edge 114 but not disposed about a corners of frame 110.

Optionally packaging unit 100 comprises at least four supports 130 that may be disposed about the corners of frame 110.

Optionally packaging 100 may comprising an even number of supports 130 equally distributed on opposite sides of frame 110.

Optionally packaging 100 may comprising an odd number of supports 130 distributed on opposite sides of frame 110 wherein opposing outer edges 114 include at least one support 130.

Optionally inner surface of holding compartment 120 along walls 126 may be configured to receive and house a dental implant. Optionally the dental implant may be packaged within a dental implant packaging for example including but not limited to a vial or any other implant holder.

Optionally frame 110 may further comprise a support skirt 116 that extends anteriorly around the outer edge 114, for example as shown in FIG. 2A-C.

FIG. 2A-C show various views of an illustrative schematic diagram of packaging unit 100 according to the present invention. FIG. 2A shows a face on posterior view of sterile sealing face 102 having a central opening 104 defining sealing face 122 of holding compartment 120, similar to that shown and described in FIG. 1C.

FIG. 2B shows a perspective anterior view of packaging unit 100 showing holding compartment 120 and supports 130, similar to that shown and described in FIG. 1B.

FIG. 2C shows a perspective view of packaging unit 100 showing the lumen of holding compartment 120 formed from wall 126.

FIG. 3A shows optional views of two packaging units 100 that are coupled in a piggy-back stacked formation. Most preferably coupling members 134, 138 are configured to couple with one another across two support members 130 of individual packaging units 100, therein forming a sealing surface buffer zone 150 provided to protect the sealing barrier 106 of packaging 100.

Figure 3C:
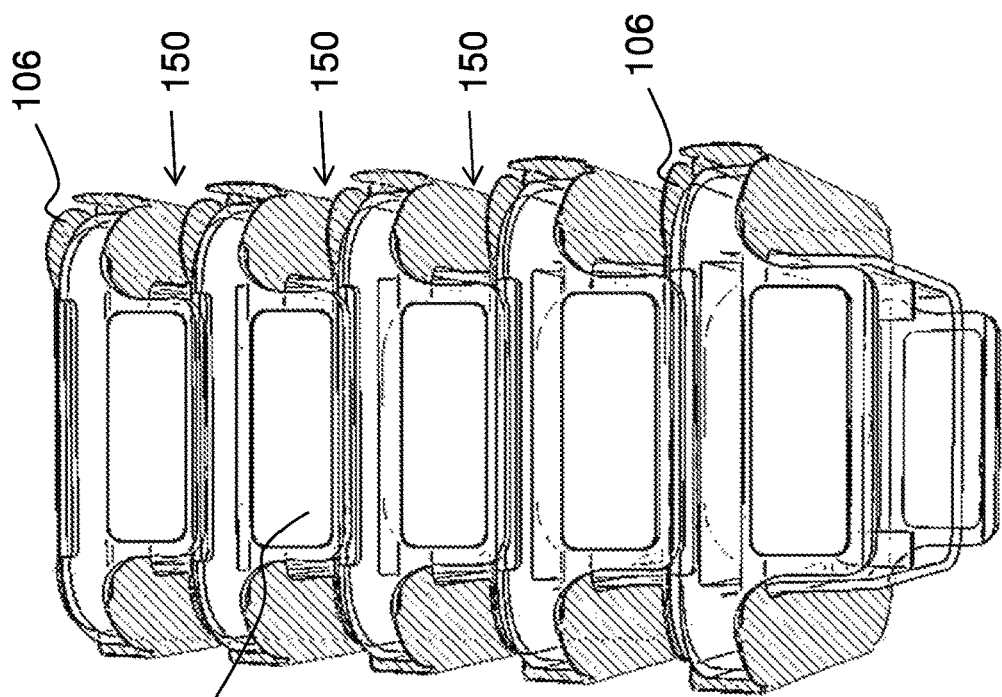
Figure 3B:
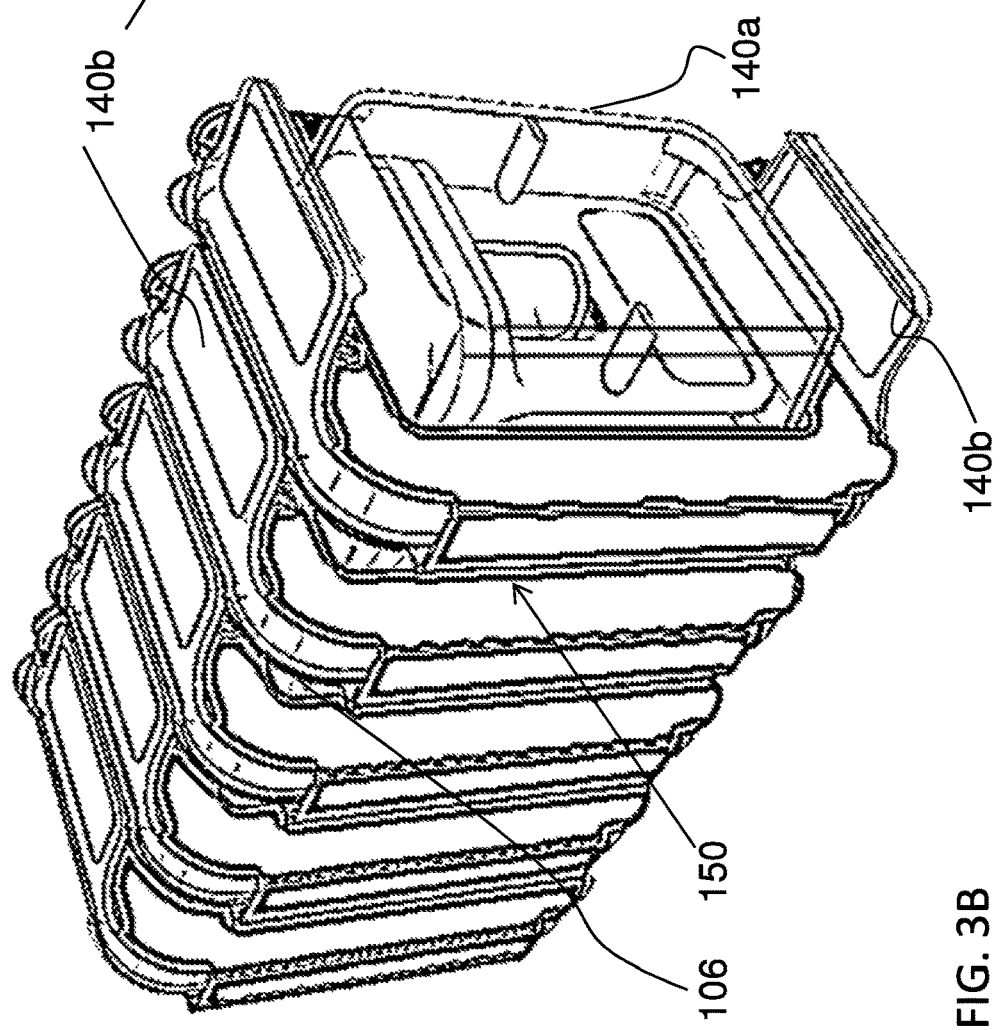

FIG. 3B-C show an illustrative perspective view of stacked packaging according to embodiments of the present invention where are plurality of packaging 100 are stacked and interlocked with one another providing at least two display surfaces 140 in the form of front or primary display surface 140*a* and secondary surfaces 140*b*, for example in the form of upper and lower display surfaces 140*b*. As show, a sterile barrier buffer zone 150 is created between two piggy-back coupled packaging that is provided to protect the sterile sealing barrier 106.

FIG. 4A-C shows perspective view of optional configuration of the support members 130 and revealing optional configuration for connection to frame body 110 wherein support members 130 extends anteriorly from outer edge 114 of frame 110 along at least a portion of the long side of frame 110. FIG. 4A-C further show optional configuration of secondary display areas 140*b*.

As shown, support surfaces 130 extend anteriorly from a portion of the long side of frame 110.

Now collectively referring to FIG. 5-8 showing an optional embodiment of the present invention for sterile packaging 200 in the form of a vial that is configured to house dental implants or the like screw form. Vials are utilized in the art to store dental implants or the like screw form bone implants, or the like contents.

Vial 200 according to embodiments of the present invention provide a sterile vial packaging that is configured to facilitate piggy-back coupling between at least two or more sterile packaging in the form of vials 200 having a vial body 202 and cap 204.

Embodiments of the present invention provide a vial 200 having a vial body 202 configured for piggy-back coupling between at least two or more vial 200. For example, a non-limiting depiction of coupling between at least two or more vials 200 are shown in FIG. 6A and FIG. 8A respectively.

Most preferably vial body 202 is configured for such piggy-back interlocking and coupling between at least two or more sterile vials 200, in that body 202 features a male-female coupling members 205, 205*m*, 205*f*, 206, 208 along the external surface of body 202.

Preferably coupling members 05, 205*m*, 205*f*, 206, 208 are disposed along the external surface of vial body 202 such that the coupling member is positioned to be perpendicular to the plane of vial cap 204 or sealing surface.

Most preferably male-female coupling members 205, 205*m*, 205*f*, 206, 208 may be disposed along the external surface of vial body 202. Optionally male-female coupling members are provided in the form of a corresponding snap fit recess, providing a female coupling member 206, and a latch, providing a male coupling member 208, that are configured to securely interlock with one another.

Optionally the male coupling member 208 and female coupling member 206 may be configured along any portion of the external surface of body 202, and configured so as to allow snap-fitting and/or coupling therebetween.

Optionally off the shelf and/or state of the art sterile implant vials may be retrofit with a vial housing 215 and/or vial external cover 210 to retrofit them with the piggy-back male-female coupling member according to the present invention, for example as shown in FIG. 6A-B and FIG. 8A-B.

FIG. 5A shows a perspective view and FIG. 5B shows a top down view, of an optional vial 200 according to embodiments of the present invention where vial body 202 features a male coupling member 208 on a first side 202*a* while the female coupling member 206 is featured on a second side 202*b*.

Optionally and preferably, second side 202*b* is disposed opposite first side 202*a* separated by about 180 degrees.

Optionally the relative angle between the male and female coupling members may be disposed at any angle relative to one another for example including but not limited to 30 degrees, 45 degrees, 90 degrees, 60 degrees, 180 degrees, the like or any combination thereof.

Optionally vial body 202 may be fit with any number of coupling members. For example, as shown in FIG. 5A-B vial 200 features three male coupling members 208 in the form of extending arms along first portion 202*a* while second side 202*b* features the corresponding female connection recess 206 configured to provide for coupling therewith, for example as shown.

Optionally male coupling members 208 as shown may assume the finger like configuration having curvature that is configured according to the size and shape of vial 200, so as to optimize coupling with female coupling member 206.

FIG. 6A shows a vial body retrofit housing 215 that features a male coupling members 208 and corresponding female coupling members 206 that are disposed on opposite sides having a separation angle of about 180 degrees, for example as shown in FIG. 5A-B. Optionally and preferably male coupling member 208 and female coupling member 206 are configured according to the shape and/or curvature of vial 200.

Preferably vial body housing 215 provides a jacket configured to fit off the shelf state of the art vial so as to retrofit such off the shelf vials with the male-female coupling capabilities according to the present invention. Preferably vial body retrofit housing 215 and/or jacket acts a sleeve to receive an off the shelf vial through a central borehole recess 215*c*.

FIG. 6B shows a vial body external retrofit cover 210 configured to fit off the shelf state of the art vial so as to retrofit such off the shelf vials with the male-female coupling capabilities according to the present invention. Cover 210 may attached and/or glued and/or otherwise securely associated along at least a portion of an off the shelf vial body. Optionally cover 210 may comprises an adhesive surface that is configured to be securely associated with the external surface of an off the shelf vial.

Most preferably the male 208 and female 206 coupling members are disposed along cover 210 in such a manner that once they are deployed onto the vial body they are disposed on opposite sides of the vial for example as shown in FIG. 5A.

Optionally cover 210 may be provided in the form of a foldable sheet.

Figure 7B:
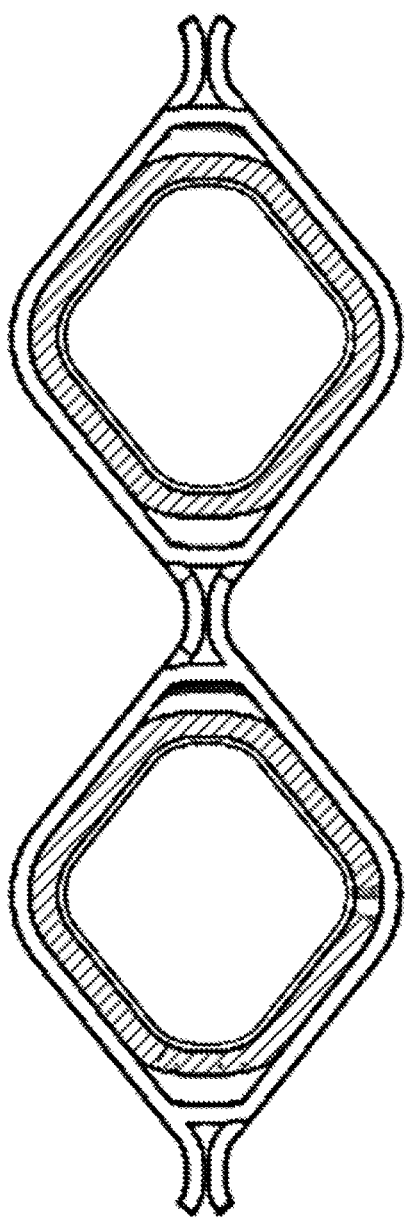
FIG. 7A-B are different views of a schematic illustrative diagram of embodiments for a packaging according to embodiments of the present invention.
Figure 7A:
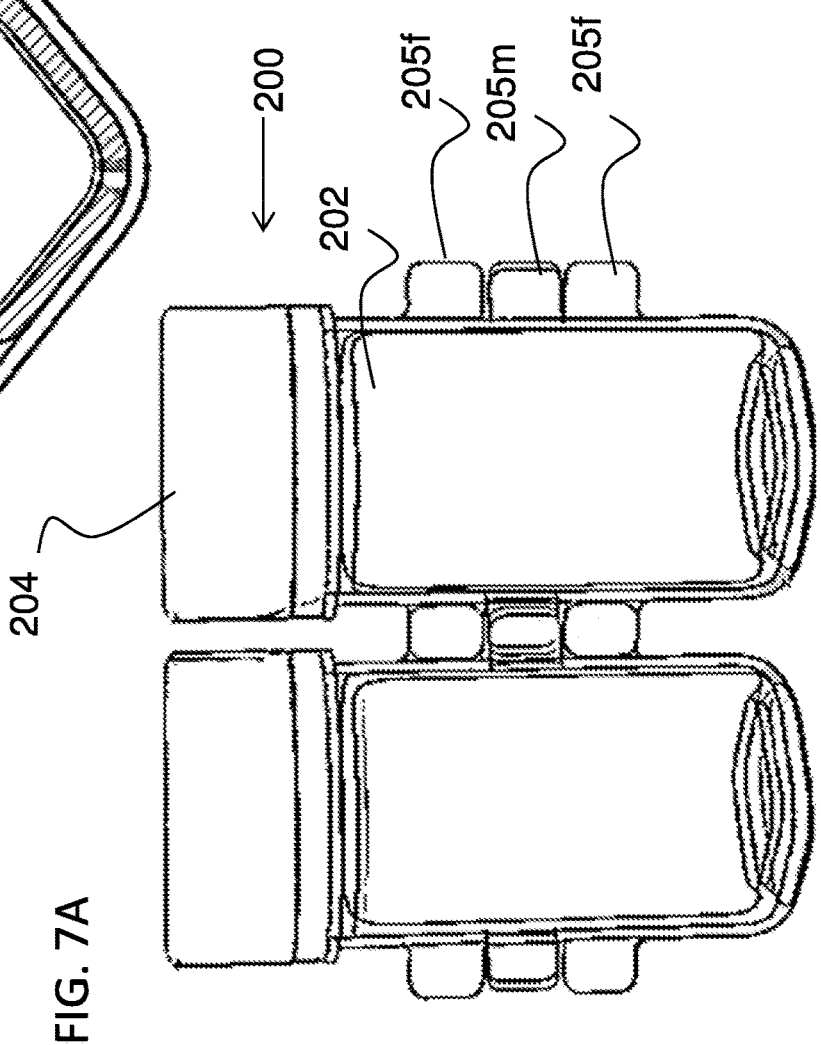

FIG. 7A-B show optional embodiments of the present invention for a vial 200 featuring a body 202 having at least two or more coupling members 205 disposed on opposite sides of vials external surface. Preferably coupling member 205 is disposed along the vial body 202 external surface such that coupling member 205 is perpendicular to the plane of vial cap 204.

Optionally and preferably each coupling member 205 is configured to have a male side 205*m*, featuring a male extension and/or latch providing a male coupling member; and a female side 205*f*, featuring a recess providing a female coupling member. Most preferably male side 205*m* and female side 205*f* are configured to correspond to one another to facilitate coupling for example as shown.

Optionally coupling members 205 may be configured to have a curvature that facilitates interlocking with adjacent coupling members 205. Optionally vial 200 may features at least one or more coupling members 205 having different curvatures.

FIG. 8A shows a vial body retrofit housing 215 that features at least two coupling member 205 having both male members 205*m* and corresponding female coupling members 205*f* that are disposed along coupling member 205, optionally about opposite sides of member 205.

Optionally and preferably the at least two coupling member 205 are disposed opposite one another along vial body 202 at angle of about 180 degrees, for example as shown.

Optionally and preferably male coupling member 205*m* and female coupling member 205*f* are configured according to the shape and/or curvature of vial 200 and member 205.

Preferably vial body housing 215 provides a jacket configured to fit off the shelf state of the art vial so as to retrofit such off the shelf vials with the male-female coupling capabilities according to the present invention. Preferably vial body retrofit housing 215 and/or jacket acts as a sleeve to receive an off the shelf vial through a central borehole recess 215*c*.

FIG. 8B shows a vial body external retrofit cover 210 configured to fit off the shelf state of the art vial so as to retrofit such off the shelf vials with the male-female coupling capabilities according to the present invention. Cover 210 may attached and/or glued and/or otherwise securely associated along at least a portion of an off the shelf vial body. Optionally cover 210 may comprises an adhesive surface that is configured to be securely associated with the external surface of an off the shelf vial.

Most preferably the at least two coupling members 205 each have at least one or more male portion 205*m* and female portion 205*f*. Most preferably coupling members 205 are disposed along cover 210 in such a manner that once they are deployed onto the vial body they are disposed on opposite sides of the vial for example as shown in FIG. 7A.

Optionally cover 210 may be provided in the form of a foldable sheet.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

While the invention has been described with respect to a limited number of embodiments, it will be appreciated that many variations, modifications and other applications of the invention may be made.

What is claimed is:

1. A first sterile packaging and a second sterile packaging, each packaging comprising:
   a) a packaging compartment configured to receive and hold contents of said packaging; the compartment defining an external surface and an internal open volume configured to receive the contents, said compartment having a surface with an open face through which said compartment may be filled with the contents, said open face forming a sterile sealing face sealed with a sterile barrier;
   b) a pair of support surfaces, said support surfaces extending anteriorly from said surface with said open face and each support surface featuring at least one coupling interface having male to female couplers configured to facilitate anterior-posterior piggy-back coupling with the other packaging thereby forming a buffer zone,
   wherein the buffer zone comprises a space completely separating the anterior-most external surface of the compartment of the first packaging and the sterile barrier of the second packaging when the first and second sterile packagings are coupled to one another by said at least one coupling interface.

2. The packaging of claim 1, wherein said support surfaces are perpendicular to said sterile sealing face.

3. The packaging of claim 1, wherein said at least one coupling interface is provided in the form of a snap fit coupling interface including a female recess member and a male latch member.

4. The packaging claim 1, comprising at least two coupling interfaces.

5. The packaging of claim 1, wherein said compartment is provided in a shape selected from the group consisting of vial, cylinder, quadrilateral, and polygon having n sides wherein n>2.

6. The packaging of claim 1, wherein said at least one coupling interface comprises a posterior female coupling member and an anterior male coupling member.

7. A sterile packaging for implants, the packaging comprising:
   a) a sterile sealing face defining a sealing face of the packaging having a frame body, the frame body having a central opening, an inner edge and an outer edge, the frame body having a width defined across said inner edge and said outer edge;
   b) said central opening defining the sealing face of a packaging compartment configured to receive and hold contents of the packaging; wherein said compartment extends anteriorly from the inner edge of said frame body; said packaging compartment having:
      i) an open face defined by said central opening;
      ii) a front surface, the front surface being a flat and even surface; and
      iii) side wall surfaces extending anteriorly from the inner edge of said frame body toward and connected to said front surface; therein defining the depth of said packaging compartment;
   c) at least two opposing packaging support surfaces each defining a substantially flat and even surface, said at least two support surfaces extending anteriorly from opposing outer edges of said frame body; each of the at least two support surfaces having a posterior edge and an anterior edge; wherein said at least two support surfaces are configured to be longer than the depth of said packaging compartment;
      i) said posterior edge is continuous with the outer edge of said frame body including a posterior coupling member disposed adjacent to said outer edge;
      ii) said anterior edge including an anterior coupling member disposed adjacent to an end of said anterior edge;
      iii) wherein said posterior coupling member and said anterior coupling member are configured to correspond with one another therein allowing for anterior-posterior piggy-back stack coupling with another adjacent such packaging therein forming a buffer zone configured to protect the sterile sealing face, the buffer zone comprising a space completely separating the anterior-most surface of the compartment and the sterile sealing face of the another adjacent such packaging, and wherein the coupled support surfaces of the coupled packages are continuous with one another defining a continuous support surface.

8. The packaging of claim 7, wherein said posterior coupling member is configured to be a female coupling member; and said anterior coupling member is configured to be a corresponding male coupling member.

9. The packaging of claim 8, wherein said posterior coupling member is configured to be a recess along the outer edge of said frame body; and wherein said anterior coupling member is configured to be a male latch member having dimensions corresponding to said recess.

10. The packaging of claim 7, wherein said posterior coupling member is configured to be a male coupling member; and said anterior coupling member is configured to be a corresponding female coupling member.

11. The packaging of claim 7, wherein the frame body has a substantially quadrilateral configuration.

12. The packaging of claim 11, wherein the frame body has a substantially rectangular configuration including two parallel long sides and two parallel short sides and wherein said support surfaces extend from the outer edge of said two parallel short sides.

13. The packaging of claim 7, comprising at least four packaging supports along said outer edge.

14. The packaging of claim 7, wherein the frame body has a design selected from the group consisting of circular, oval, and ellipsoid.

15. The packaging of claim 7, wherein the inner surface of the packaging compartment is configured to receive and house a dental implant.

16. The packaging of claim 15, wherein said inner surface of the packaging compartment is configured to receive and house a dental implant packed within a container.

17. The packaging of claim 16, wherein said inner surface of the packaging compartment is configured to receive and house a packed dental implant provided in a container in the form of a dental implant vial.

18. The packaging of claim 7, wherein said frame body further comprises a skirt extending from the outer edge.

\* \* \* \* \*